United States Patent
Arcasoy et al.

(10) Patent No.: US 8,273,551 B2
(45) Date of Patent: Sep. 25, 2012

(54) USE OF CYTOKINE RECEPTORS AS BIOMARKERS AND THERAPEUTIC TARGETS IN HUMAN CANCER

(75) Inventors: Murat O. Arcasoy, Chapel Hill, NC (US); Zishan A. Haroon, Ironwood, MI (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/169,641

(22) Filed: Jun. 27, 2011

(65) Prior Publication Data

US 2011/0256543 A1     Oct. 20, 2011

Related U.S. Application Data

(62) Division of application No. 12/542,229, filed on Aug. 17, 2009, now abandoned, which is a division of application No. 11/512,501, filed on Aug. 30, 2006, now Pat. No. 7,598,057, which is a division of application No. 10/625,137, filed on Jul. 23, 2003, now Pat. No. 7,160,697.

(60) Provisional application No. 60/404,870, filed on Aug. 21, 2002.

(51) Int. Cl.
*C12N 15/00* (2006.01)
*C07H 21/04* (2006.01)
*C07K 14/00* (2006.01)

(52) U.S. Cl. ........................ 435/69.1; 536/23.5; 530/350

(58) Field of Classification Search ........................ None
See application file for complete search history.

(56) References Cited

U.S. PATENT DOCUMENTS 5,378,808 A   1/1995   D'Andrea et al.
7,745,391 B2   6/2010   Mintz et al.

OTHER PUBLICATIONS

International Search Report for PCT/US03/27368, Jun. 29, 2007.
Arcasoy M O, et al. Expression of erythropoietin receptor splice variants in human cancer. Biochemical and Biophysical Research Communications. 2003. vol. 307, pp. 999-1007.
Acs G, et al. Erythropoietin and Erythropoietin Receptor Expression in Human Cancer. Cancer Research. May 1, 2001. vol. 61, pp. 3561-3565.
Mittelman M, et al. Analysis of the erythropoietin receptor gene in patients with myeloproliferative and myelodysplastic syndromes. Leukemia Research. 1996. vol. 20, No. 6, pp. 459-466.
Eck S L and Wilson J M. 1996, in: Goodman and Gilman's The Pharmacological Basis of Therapeutics, Ninth Edition, McGraw-Hill, New York.
Noguchi et al., Cloning of the Human Erythropoietin Receptor Gene, *Blood*, vol. 78, No. 10:2548-2558 (1991).
Nakamura et al., A Truncated Erythropoietin Receptor That Fails to Prevent Programmed Cell Death of Erythoid Cells, *Science*, vol. 257:1138-1141 (Aug. 21, 1992).
Amgen, Inc. Influence of ethrythropoietic stimulating agents (ESAS) on tumor progression and survival. 2007 ODAC Meeting Information Package, pp. 127-203.
Eck SL and Wilson JM, 1996, in: Goodman & Gilman's The Pharmacological Basis of Therapeutics, Ninth Edition, McGraw-Hill, New York.

*Primary Examiner* — Xiaozhen Xie
(74) *Attorney, Agent, or Firm* — Myers Bigel Sibley & Sajovec, P.A.

(57) ABSTRACT

Nucleic acids encoding erythropoietin receptor isoforms are described, as well as the encoded isoforms, methods of detecting the same, and methods of screening for and treating cancer.

5 Claims, 2 Drawing Sheets

Intron 6 insert (Isoform 1)

exon 6 ⟵⎤               intron 6 insert
... CAC CGC CGg atg gtc agg gaa ggc tcc agg agg agg tga cat cag agt gga aac
    His   Arg   Arg Met Val Arg Glu Gly Ser Arg Arg Arg End ctg aag att gga agg aag cag ccg ctt gaa aag tgg gga gaa gaa aca gca agt gca ⎡⟶ exon 7
       aag gcc ctg agG GCT CT ...

Intron 7 insert (Isoform 2)

exon 7    ⟵⎤  intron 7 insert  ⎡⟶    exon 8
...GGT AAC TTC CAG gtt ggt gct att tct tca gCT GTG GCT GTA CCA GAA TGA ...
   Gly  Asn  Phe  Gln  Val Gly Ala Ile Ser Ser Ala  Val  Ala  Val  Pro  Glu  End

Intron 7 unspliced (Isoform 3)

exon 7 ⟵⎤                         intron 7
...TTC CAG gta ggt ggc ctg gtt gtc ccc tca gtg cct ggg ctt ccc tgc ttc ttg cag cca
   Phe  Gln   Val Gly Gly Leu Val Val Pro Ser Val Pro Gly Leu Pro Cys Phe Leu Gln Pro ⎡⟶  exon 8
       aac tgc agg cct ctc tga gca ggt tgg tgc tat ttc ttc agC TGT GGC TGT ...
       Asn  Cys  Arg  Pro Leu End

Intron 5 unspliced (Isoform 4)

exon 5  ⟵⎤                        intron 5
...CCT AGC Ggt gag gcc cca ggc ggg ggt gta gga gga gcc agg gcg aat cac ggg
   Pro   Ser   Gly Glu Ala Pro Gly Gly Gly Val Gly Gly Ala Arg Ala Asn His Gly ⎡⟶  exon 6
   gca agc cca ccg ccc tga cct cct ccc cgc ctc tta gAC CTG ...
   Ala Ser  Pro  Pro  Pro  End

Exon 6 skipped (Isoform 5)

exon 5   ⟵⎯⎡⟶  exon 7
... ACG CCT AGC GGG CTC TGA AGC AGA ...
   Thr   Pro   Ser   Gly   Leu  End

FIGURE 2

USE OF CYTOKINE RECEPTORS AS BIOMARKERS AND THERAPEUTIC TARGETS IN HUMAN CANCER

RELATED APPLICATIONS

This application claims priority to and is a divisional of U.S. patent application Ser. No. 12/542,229, filed Aug. 17, 2009, now abandoned, which is a divisional of U.S. patent application Ser. No. 11/512,501, filed Aug. 30, 2006, now U.S. Pat. No. 7,598,057, which is a divisional of U.S. patent application Ser. No. 10/625,137, filed Jul. 23, 2003, now U.S. Pat. No. 7,160,697, which claims the benefit of Provisional Application Ser. No. 60/404,870, filed Aug. 21, 2002, the disclosures of each of which are hereby incorporated herein by reference in their entirety.

FIELD OF THE INVENTION

The present invention concerns nucleic acids encoding erythropoietin receptor isoforms, proteins encoded by such nucleic acids, antibodies that bind to such proteins, and methods of using the same.

BACKGROUND OF THE INVENTION

Erythropoietin (Epo) is the principal hematopoietic growth factor that promotes the viability, differentiation and proliferation of mammalian erythroid progenitor cells (S. Krantz, *Blood* 77, 419-34 (1991)). The biologic effects of Epo are mediated via its interaction with its specific transmembrane receptor, EpoR (H. Youssoufian, *Blood* 81, 2223-36 (1993)). The EpoR lacks intrinsic tyrosine kinase activity and upon ligand binding activates a receptor-associated tyrosine kinase Jak2 which is critical for anti-apoptosis and mitogenic signaling via the EpoR (0. Miura et al., *Blood* 84, 1501-7 (1994); B. Witthuhn et al., *Cell* 74, 227-36 (1993); J. Ihle, *Nature* 337, 591-4 (1995); H. Zhuang et al., *J. Biol Chem.* 270, 14500-4 (1995)). Activated Jak2 then phosphorylates a number of cytoplasmic proteins as well as the EpoR itself. Expression of Epo receptors has been reported on several non-hematopoietic cell types including vascular endothelial cells, placental tissue, neuronal cells, kidney and cardiomyocytes (A. Anagnostou et al., *Proc. Natl. Acad. Sci. USA* 91, 3974-8 (1994); S. Masuda et al., *J. Biol. Chem.* 268, 112-8-16 (1993); S. Sawyer et al., *Blood* 74, 103-9 (1989); M. Wald et al., *J. Ce. Physiol.* 167, 461-8 (1996)).

Recombinant human Epo (r-HuEpo) has been widely used in many different types of cancers for the treatment or prevention of chemo-radiotherapy induced anemia (A. Moliterno and J. Spivak, *Hematol. Oncol. Clin. North Am.* 10, 345-63 (1996)). For instance, in patients with breast cancer, r-HuEpo has been investigated in clinical trials for its potential beneficial effects in the prevention or treatment of chemotherapy or radiation therapy-related anemia (L. Del Mastro et al., *J. Clin. Oncol.* 15, 2715-21 (1997); H. Ludwig et al., *Ann. Oncol.* 4, 161-7 (1993); P. Sweeney et al., *Br. J Cancer* 77, 1996-2002 (1998); S. Vijayakumar et al., *Int. J. Radiat. Oncol. Biol. Phys* 26, 721-9 (1993)), for mobilization of peripheral blood progenitor cells (C. Waller et al., *Bone Marrow Transplant* 24, 19-24 (1999)), to increase the rate of hematopoietic recovery following high dose chemotherapy (P. Benedetti Panici et al., *Br. J Cancer* 75, 1205-12 (1997); S. Filip et al., *Neoplasma* 46, 166-72 (1999)) as well as use in ex vivo expansion strategies of stem cells (C. Bachier et al., *Exp Hematol.* 27, 615-23 (1999); L. Pierelli et al., *Exp. Hematol.* 27, 416-24 (1999); P. Stiff et al., *Blood* 95, 2169-74 (2000); W. Vogel et al., *Blood* 86, 1362-7 (1996)). Similarly, r-HuEpo has been investigated in several clinical trials of squamous cell cancers of head-neck (F. Dunphy et al., *Cancer* 86, 1362-7 (1999); M. Henke et al., *radiother Oncol* 50, 185-90 (1999); G. Mantovani et al., *Oncol. Rep.* 6, 421-6 (1999)) and uterine cervix (K. Dusenbery et al., *Int. J. Radiat. Oncol. Biol. Phys*. 29, 1079-84 (1994)).

In view of the foregoing, it would be extremely desirable to understand the association of Epo with tumor growth and how EpoR may be involved in cancer pathophysiology and progression.

SUMMARY OF THE INVENTION

A first aspect of the present invention is an isolated nucleic acid encoding erythropoietin isoform 1, erythropoietin isoform 2, erythropoietin isoform 3, erythropoietin isoform 4, or erythropoietin isoform 5, or a nucleic acid that encodes the opposite or complementary strand of a nucleic acid as set forth above (e.g., a DNA encoding an RNA).

A second aspect of the present invention is a protein encoded by a nucleic acid as described above (e.g., an isolated and/or purified protein).

A third aspect of the present invention is an antibody that selectively or specifically binds to a protein as described above.

A further aspect of the present invention is an oligonucleotide probe that selectively or specifically binds to a nucleic acid as described above.

A further aspect of the present invention is a method of screening a subject for cancer, comprising: detecting the presence or absence of a nucleic acid encoding an isoform as described above in the subject, the presence of such a nucleic acid indicating the subject is afflicted with or at risk of developing cancer.

A further aspect of the present invention is a method of screening a subject for cancer, comprising detecting the presence or absence of a protein or isoform as described above in the subject, the presence of such a protein indicating the subject is afflicted with or at risk of developing cancer.

Particular cancers which may be screened by the methods described herein include, but are not limited to, breast, cervix, ovarian, prostate, colon and lung cancer.

The foregoing and other objects and aspects of the present invention are explained in detail in the drawings herein and the specification set forth below.

BRIEF DESCRIPTION OF THE DRAWINGS

FIG. 2. Changes in the open reading frames (ORFs) of mature mRNA sequences from the full-length wild-type receptor in the isoforms of EpoR described herein. Isoform 1 (SEQ ID NO: 4): Additional nucleotides from intron 6 (nucleotides 5949-6062, SEQ ID NO: 1) are spliced between exons 6 and 7. Isoform 2 (SEQ ID NO: 6): Splicing at the 5' end of exon 8 occurs 19 nucleotides upstream (nucleotide 7498) from that seen in the full-length wild-type message (nucleotide 7517). Isoform 3 (SEQ ID NO: 8): Intron 7 is not spliced out of the final message. Isoform 4 (SEQ ID NO: 10): Intron 5 is not spliced out of the final message. Isoform 5 (SEQ ID NO: 12): exon 6 is skipped, with exon 5 spliced directly to exon 7. Putative C-terminal amino acid sequence changes from wild-type EpoR are depicted in bold.

DETAILED DESCRIPTION OF THE PREFERRED EMBODIMENTS

Figure 1:
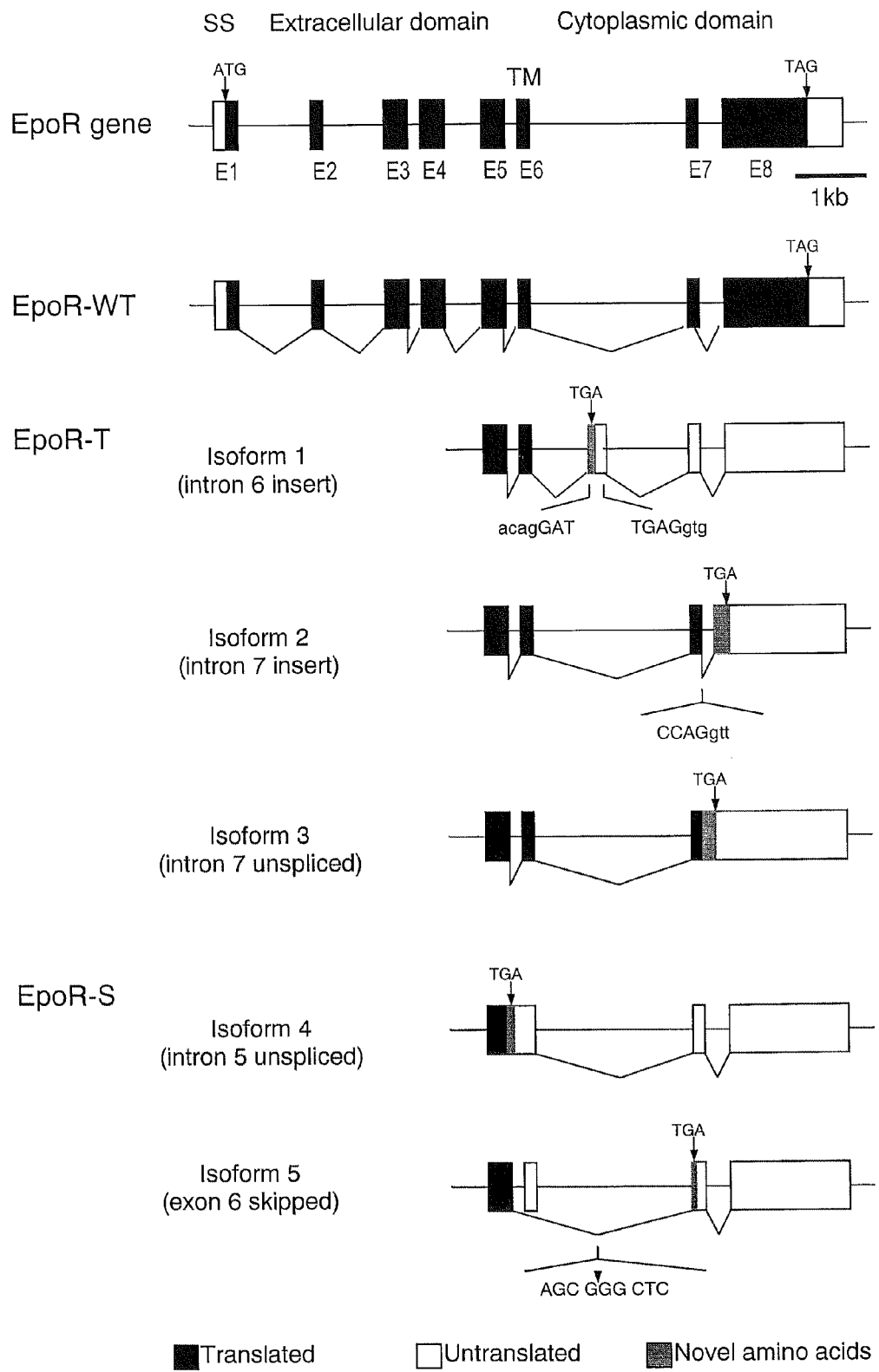
FIG. 1. The organization of the EpoR gene (GenBank accession number S45332, SEQ ID NO: 1). The splicing that results in the mature mRNA for the wild-type receptor (SEQ ID NO: 3), and five alternatively spliced isoforms (1-5) described herein are depicted schematically. The translated regions of the gene are indicated in black, whereas untranslated regions are indicated in white. Novel amino acid translations that result from alternative splicing of the EpoR gene transcript are indicated in grey.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Nucleic acid as used herein refers to any type of nucleic acid, including naturally occurring and synthetic nucleic acids and including both DNA and RNA.

Subjects with which the present invention may be carried out are generally mammalian subjects, including both human subjects and non-human subjects (e.g., dog, cat, horse, rabbit, rat) for veterinary or research purposes.

Any type of antibody may be used in the present invention. The term "antibodies" as used herein refers to all types of immunoglobulins, including IgG, IgM, IgA, IgD, and IgE. Of these, IgM and IgG are particularly preferred. The antibodies may be monoclonal or polyclonal (with monoclonal antibodies preferred) and may be of any species of origin, including (for example) mouse, rat, rabbit, horse, or human. See, e.g., M. Walker et al., *Molec. Immunol.* 26, 403-11 (1989). Antibody fragments that retain specific binding to the protein or epitope bound by the antibody are included within the scope of the term "antibody" and include, for example, Fab, F(ab')2, and Fc fragments, and the corresponding fragments obtained from antibodies other than IgG. Such fragments can be produced by known techniques. The antibodies may be chimeric or humanized, particularly when they are used for therapeutic purposes.

Applicants specifically intend that all United States patent references cited herein be incorporated herein by reference in their entirety.

1. Nucleic Acids.

As noted above, a first aspect of the present invention is a nucleic acid encoding an erythropoietin receptor isoform as described herein. In certain embodiments the nucleic acid may be an RNA such as an mRNA, or may be a DNA.

In one embodiment, the nucleic acid encodes erythropoietin receptor isoform 1 and has the sequence, given herein as SEQ ID NO: 4.

In another embodiment, the nucleic acid encodes erythropoietin receptor isoform 2 and has the sequence given herein as SEQ ID NO: 6.

In another embodiment, the nucleic acid encodes erythropoietin receptor isoform 3 and has the sequence given herein as SEQ ID NO: 8.

In another embodiment, the nucleic acid encodes erythropoietin receptor isoform 4 and has the sequence given herein as SEQ ID NO: 10.

In another embodiment, the nucleic acid encodes erythropoietin receptor isoform 5 and has the sequence given herein as SEQ ID NO: 12.

In another embodiment, the nucleic acid that encodes the opposite strand of a nucleic acid as set forth above (e.g., is a DNA encoding an RNA).

Nucleic acids as described above may be natural or synthetic, and can be produced in accordance with techniques known in the art or variations thereof which will be apparent in light of the disclosure herein.

Nucleic acids as described above may be coupled to appropriate regulatory elements such as a promoter to produce a recombinant nucleic acid construct, which construct may be inserted into a host cell in which the promoter is operable so that the encoded protein is expressed by the host cell. Recombinant techniques and the production of proteins in recombinant cells may be carried out in accordance with known techniques.

2. Antibodies.

Polyclonal antibodies used to carry out the present invention may be produced by immunizing a suitable animal (e.g., rabbit, goat, etc.) with the antigen to which the monoclonal antibody binds, collecting immune serum from the animal, and separating the polyclonal antibodies from the immune serum, in accordance with known procedures. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies of the present invention may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256: 495-497; Kozbor, D. et al. (1985) *J. Immunol. Methods* 81:31-42; Cote, R. J. et al. (1983) *Proc. Natl. Acad. Sci.* 80:2026-2030; Cole, S. P. et al. (1984) *Mol. Cell Biol.* 62:109-120). Briefly, the procedure is as follows: an animal is immunized with antigen or immunogenic fragments or conjugates thereof. For example, haptenic oligopeptides of antigen can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Human hybridomas which secrete human antibody can be produced by the Kohler and Milstein technique. Although human antibodies are especially preferred for treatment of human, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al., *Bio Techniques* 4(4):214-221 (1986); L. K. Sun et al., *Hybridoma* 5 (1986).

In addition, techniques developed for the production of "chimeric antibodies", the splicing of mouse antibody genes to human antibody genes to obtain a molecule with appropriate antigen specificity and biological activity can be used (S. L. Morrison, et al. *Proc. Natl. Acad. Sci.* 81, 6851-6855 (1984); M. S. Neuberger et al., *Nature* 312:604-608 (1984); S. Takeda, S. et al., *Nature* 314:452-454 (1985)). Alternatively, techniques described for the production of single chain antibodies may be adapted, using methods known in the art, to produce isoform-specific single chain antibodies. Antibodies with related specificity, but of distinct idiotypic composition, may be generated by chain shuffling from random combinatorial immunoglobin libraries (D. R. Burton, *Proc. Natl. Acad. Sci.* 88, 11120-3 (1991)).

Antibodies may also be produced by inducing in vivo production in the lymphocyte population or by screening immunoglobulin libraries or panels of highly specific binding reagents as disclosed in the literature (R. Orlandi et al., *Proc. Natl. Acad. Sci.* 86, 3833-3837 (1989)); G. Winter et al., *Nature* 349, 293-299 (1991)).

Antibodies that selectively bind to a particular erythropoietin receptor isoform as described herein (i.e., that selectively bind to one of isoforms 1-5 but do not bind to the other of isoforms 1-5) can be identified in accordance with known techniques, such as their ability to compete with labeled antibody to in binding to that isoform in a competitive binding assay.

If desired, antibodies specific for a particular isoform can be used to produce anti-idiotypic (paratope-specific) antibodies. See e.g., McNamara et al., *Science* 220, 1325-26 (1984), R. C. Kennedy, et al., *Science* 232, 220 (1986).

3. Immunoassay Techniques.

Those skilled in the art will be familiar with numerous specific immunoassay formats and variations thereof which may be useful for carrying out the method disclosed herein. See generally E. Maggio, Enzyme-Immunoassay, (1980)(CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies as described herein may be coupled or conjugated to a solid support suitable for a diagnostic assay (e.g., beads, plates, slides or wells formed from materials such as latex or polystyrene) in accordance with known techniques, such as precipitation. Antibodies as described herein may likewise be coupled or conjugated to detectable groups such as radiolabels (e.g., $^{35}$S, $^{125}$I, $^{131}$I), enzyme labels (e.g., horseradish peroxidase, alkaline phosphatase), fluorescent labels (e.g., fluorescein), chemiluminescent labels (e.g., acridinium groups, metalloporphyrins such as phthalocyanine dyes, luminol, etc.), metal atoms (e.g., technetium-99m), etc., in accordance with known techniques. See, e.g., U.S. Pat. No. 4,472,509 to Gansow (metal chelates to monoclonal antibodies); U.S. Pat. No. 5,061,641 to Schochat et al.; and U.S. Pat. No. 4,861,869 to Nicoleotti et al. (radiolabelling proteins).

Immunoassays, or other types of assays to detect and/or quantitate the level of the isoform in samples as described below, may be used in screening assays to detect pathologic states associated with aberrant levels of isoform expression (e.g., tumors, inflammatory states), diagnostic studies, prognostic studies, or to monitor the progression or diminution of isoform expression in correlation with disease state.

Samples that may be collected for use in carrying out the immunoassay may be tissue samples from the organ or tissue of interest within the subject, such tissue generally of most interest being those types of tissues/cells that express differing amounts of isoform in pathologic states as compared to non-pathologic states, or biological fluids such as blood (including blood fractions such as blood plasma or blood serum), urine, cerebrospinal fluid, etc). Examples may include overexpression or aberrant expression of the isoform in various types of malignancies (e.g ovarian cancer, endometrial cancer, pancreatic cancer, breast cancer, urinary bladder cancer, lung cancer, etc.), as well as overexpression or aberrant expression in other pathologic states.

A biological sample may be a cell sample, with an intervening culturing step being performed between the time the cell sample is collected from the subject and the immunoassay is carried out on the biological sample.

For immunohistological techniques, a tissue sample is collected from the subject, and the presence or absence of binding of an antibody of the invention is detected. The presence of binding of the antibody in an abnormal pattern or a pattern indicative of a tumor or cancer indicates the presence of a tumor or cancer in the subject from which the tissue sample is collected. The presence of the antigen in a metastatic tumor deposit can also be used to determine a likely source of the primary tumor. Any suitable immunohistology format may be used. The tissue sample may include patient biopsies, resections or cells for cytologic study. A similar technique to immunohistology is the use of similar techniques to detect and/or phenotype cells in body fluids or other suspensions as is used for flow cytometric examination.

For in vivo diagnostic purposes the antibody according to the invention is coupled to or provided with a suitable externally detectable label, such as e.g. a radiolabel as described above or a metal atom (e.g., technetium-99m), and administered to a subject (e.g., by intravenous or intraarterial injection), in an amount sufficient to produce an externally detectable signal, whereupon the possible localized accumulation of antibody in the body is determined, with a localized accumulation of the antibody (in a region other than that which would ordinarily be expected for normal subjects or subjects free of disease) indicating the present of a tumor in that subject.

4. Nucleic Acid Assay Techniques.

Detection of mRNAs specific to EpoR isoforms 1, 2, 3, 4, and 5 may be carried out by any suitable technique, including but not limited to using reverse transcriptase-polymerase chain reaction (RT-PCR) amplification with isoform-specific primers and Southern blot analysis of the resulting RT-PCR amplicons. For example, PolyA$^+$ RNA may be isolated by any technique known by those skilled in the art from patients patient cells and/or cancer cells, including but not limited to breast, colon, lung, ovary, and prostate cells or cancer cells. Methods for RT-PCR amplification of the isolated RNA are known in the art and may be carried out using EpoR isoform-specific primer pairs, preferably as described below.

Oligonucleotide probes (or primers) that specifically bind to a nucleic acid encoding an isoform as described above (including the opposite strands thereof), and pairs of probes (where at least one member of the pair is specific for a nucleic acid encoding one particular isoform), are also an aspect of the present invention. In general, such probes are from 8 or 10 nucleic acids in length up to 40 or 50 nucleic acids in length, or more. By "specifically bind" is meant that a probe binds to a nucleic acid (or complement thereof) that encodes one isoform as described herein, but does not bind to a nucleic acid (or complement thereof) that encodes another isoform as described herein. Probes may optionally be labeled with a detectable group such as a radioisotope, enzyme, or member of a binding pair in some assay formats. Where a pair of probes or primers is used for amplification, it will be appreciated that only one member of the pair need be isoform-specific, and that the other member of the pair may be one which will bind to nucleic acids encoding more than one of the isoforms described herein, so long as the primer pair specifically amplifies only nucleic acid encoding one of the isoforms described herein. Examples of such oligonucleotide probes, and pairs thereof, are as follows:

Primer Pair Specific for Intron 6 Insert (Isoform 1)

```
                                              (SEQ ID NO: 14)
28AS:: 5' TCA AGC GGC TGC TTC CTT CCA A 3'

(SEQ ID NO: 15)
ER4-5: 5' GCA GGG AGC GTA CAG AGG GTG GAG 3'
```

Primer Pair Specific for Intron 7 Insert (Isoform 2)

```
                                              (SEQ ID NO: 16)
33AS:  5' GAA GAA ATA GCA CCA ACC TGG AAG 3'

(SEQ ID NO: 17)
31S:   5' CTG ACG CCT AGC GAC CTG GAC C 3'
```

Primer Pair Specific for Intron 7 Unspliced (Isoform 3)

```
                                              (SEQ ID NO: 18)
31AS:  5' GCA GTT TGG CTG CAA GAA GCA 3'

(SEQ ID NO: 17)
31S:   5' CTG ACG CCT AGC GAC CTG GAC C 3'
```

Primer Pair Specific for Intron 5 Unspliced (Isoform 4)

```
                                              (SEQ ID NO: 19)
26S:   5' GGA GCC AGG GCG AAT CAC GG 3'

(SEQ ID NO: 20)
32S:   5' GCC TTC AAA CTC GCT CTC TG 3'
```

Primer Pair Specific for Exon 6 Skipped (Isoform 5)

```
                                              (SEQ ID NO: 21)
34AS   5' GCT TCA GAG CCC GCT AGG CGT 3'

(SEQ ID NO: 15)
ER4-5  5' GCA GGG AGC GTA CAG AGG GTG GAG 3'
```

Note that, in the foregoing pairs, the primers of SEQ ID NO. 14, 16, 18, 19 and 21 are specific for the identified isoform, and the primers of SEQ ID NO. 15, 17 and 20 are not specific. In, each pair, only one primer need be specific to provide an isoform-specific primer pair.

Blotting techniques are well known in the art. See, e.g.; Sambrook et al., *Molecular Cloning: a Laboratory Manual* 3rd Ed. (Cold Spring Harbor, N.Y.); Ausubel et al. *Current Protocols in Molecular Biology* (Green Publishing Associates, Inc. and John Wiley & Sons, Inc., New York). The nucleic acids resulting from RT-PCR amplification may be separated by gel electrophoresis and immobilized on a suitable matrix, e.g. a filter of nitrocellulose. The presence of target sequences among the amplification products may be shown by incubation of the blotted amplicons with a probe (usually labeled) under conditions that promote denaturation and rehybridization. Because the probe is designed to base pair with target sequences, the probe will bind under renaturing conditions. Unbound probe is then removed, and detection of target sequences may be accomplished via known techniques to detect the labeled probe.

The present invention and the various methods and compounds therein are explained in greater detail in the following non-limiting examples.

EXAMPLE 1

The Erythropoietin Receptor (EpoR) gene. The human EpoR gene has been cloned and sequenced as previously described (Noguchi et al. (1991) *Blood* 78:2548-2556). The gene spans 8.6 kilobases, and comprises of 8 exons with 7 intervening introns, the latter of which range in size from 81 bp to 2.1 kb. The organization of the EpoR gene is outlined in FIG. 1. The full-length wild-type form of EpoR comprises of 508 amino acids (SEQ ID NO: 2) in three domains: extracellular, transmembrane (TM), and cytoplasmic. Exons 1-5 encode for the extracellular domain of EpoR, exon VI encodes for the transmembrane domain, while exons VII and VIII encode for the cytoplasmic domain of the receptor. In the examination of EpoR expression in tumor vasculature, analysis by RT-PCR indicated a high level of EpoR mRNA expression in breast cancer cells, as well as squamous cell cancers of head-neck and uterine cervix was observed.

EXAMPLE 2

Novel Isoforms of EpoR mRNA Transcripts. The resulting RT-PCR amplification products derived from human cervix, breast, prostate, and ovarian cancer cell lines were sequenced and analyzed. The results of this study revealed five alternatively spliced EpoR mRNA transcripts that differ from the mature, full-length wild-type EpoR mRNA. Using isoform-specific PCR primers, transcripts corresponding to each isoform were detected in breast, colon, lung, ovarian and prostate cancer. The organization of these five isoforms is outlined in FIG. 1. The alternative forms of EpoR predicted to be coded for from these alternatively spliced mRNAs fall into two categories. Isoforms 1, 2, and 3 are described as truncated (EpoR-T), and possess the extracellular and transmembrane domains of the wild-type receptor, while lacking portions of the cytoplasmic domain. Isoforms 4 and 5 are described as soluble (EpoR-S), and only possess the extracellular domain of the wild-type receptor intact. The changes in the putative C-terminal amino acid sequence encoded by these mRNAs are outlined in FIG. 2.

EXAMPLE 3

EpoR Isoform 1. The mRNA that codes for Isoform 1 contains an additional 114 nucleotides from intron 6 (nucleotides 5949-6062, SEQ ID NO: 1) spliced between exons 6 and 7. The resulting mRNA will code for an EpoR peptide 285 amino acids in length (SEQ ID NO: 5) with a severe truncation in the cytoplasmic region. At the C-terminal, 9 novel amino acids (M V R E G S R R R STOP) inserted at position 277 of the full-length EpoR peptide sequence.

EXAMPLE 4

EpoR Isoform 2. The mRNA that codes for Isoform 2 is the result of an alternative splicing event between the 3' end of exon 7 and 5' end of exon 8, in which an additional 19 nucleotides (nucleotides 7498-7516, SEQ ID NO: 1) are added to the 5' end of exon 8. The mRNA from this splicing event codes for an EpoR peptide 317 amino acids in length (SEQ ID NO: 7) with a severe truncation in the cytoplasmic domain, in which 12 novel amino acids (V G A I S S A V A V P E STOP) are inserted at position 306 of the EpoR peptide sequence. As with Isoform 1, Isoform 2 also possesses a truncation of the cytoplasmic domain of the full-length peptide sequence of EpoR.

EXAMPLE 5

EpoR Isoform 3. The translation of isoform 3 results from a processed EpoR mRNA in which sequences from intron 7 (nucleotides 7422-7516, SEQ ID NO: 1) are not spliced out of the final message. The resulting translation is a 328 amino acid peptide (SEQ ID NO: 9), with 23 novel amino acids introduced to the C-terminus (V G G L V V P S V P G L P C F L Q P N C R P L STOP) at position 306 of the EpoR peptide sequence. As with Isoforms 1 and 2, Isoform 3 possesses a truncation of the cytoplasmic domain of the full-length peptide sequence of EpoR. The sequence of the ORF of the mRNA message (SEQ ID NO: 8) and the peptide sequence of EpoR Isoform 3 (SEQ ID NO: 9) is identical to the translation predicted from an mRNA described previously (Nakamura et al. (1992) *Science* 257:1138-1141).

EXAMPLE 6

EpoR Isoform 4. The processed EpoR mRNA that translates into Isoform 4 contains sequences from intron 5 (nucleotides 5061-5144, SEQ ID NO: 1) are not spliced out of the final message. The resulting translation is a 267 amino acid peptide (SEQ ID NO: 11) with 21 novel amino acids (G E A P G G G V G G A R A N H G A S P P P STOP) introduced to the C-terminus at position 247 of the full-length EpoR peptide sequence. This isoform of EpoR possesses neither the transmembrane nor cytoplasmic domains of the full-length receptor. The translation that codes for Isoform 4 results in a soluble form of EpoR, containing the extracellular domain of the receptor only.

EXAMPLE 7

EpoR Isoform 5. Isoform 6 is a translation that results from the alternatively processed EpoR mRNA in which sequences from exon 6 are skipped, i.e. exons 5 and 7 are spliced together directly. The translation of this message results in a 248 amino acid peptide (SEQ ID NO: 13), in which 2 novel amino acids (G L STOP) are introduced at position 247 of the full-length peptide sequence of EpoR. As with Isoform 4, Isoform 5 of EpoR is a soluble form of the receptor that comprises of only the extracellular domain.

The foregoing is illustrative of the present invention, and is not to be construed as limiting thereof. The invention is defined by the following claims, with equivalents of the claims to be included therein.

That which is claimed is:

1. An isolated nucleic acid selected from the group consisting of
   a nucleic acid encoding erythropoietin receptor isoform 4 and having the sequence given herein as SEQ ID NO: 10; and
   a nucleic acid that is the full length complement of SEQ ID NO: 10.

2. The nucleic acid according to claim 1 encoding erythropoietin receptor isoform 4 and having the sequence given herein as SEQ ID NO: 10.

3. The nucleic acid according to claim 1, wherein said nucleic acid is an RNA.

4. A recombinant nucleic acid comprising a promoter operatively associated with a nucleic acid according to claim 1.

5. An isolated host cell containing a recombinant nucleic acid according to claim 4 and which expresses the encoded erythropoietin receptor isoform.

* * * * *

SEQUENCE LISTING

```
<160> NUMBER OF SEQ ID NOS: 21

<210> SEQ ID NO 1
<211> LENGTH: 8647
<212> TYPE: DNA
<213> ORGANISM: Homo sapiens
<220> FEATURE:
<221> NAME/KEY: CDS
<222> LOCATION: (1916)..(2030)
<223> OTHER INFORMATION: exon 1
<220> FEATURE:
<221> NAME/KEY: CDS
<222> LOCATION: (2887)..(3022)
<223> OTHER INFORMATION: exon 2
<220> FEATURE:
<221> NAME/KEY: CDS
<222> LOCATION: (4010)..(4185)
<223> OTHER INFORMATION: exon 3
<220> FEATURE:
<221> NAME/KEY: CDS
<222> LOCATION: (4266)..(4423)
<223> OTHER INFORMATION: exon 4
<220> FEATURE:
<221> NAME/KEY: CDS
<222> LOCATION: (4907)..(5060)
<223> OTHER INFORMATION: exon 5
<220> FEATURE:
<221> NAME/KEY: CDS
<222> LOCATION: (5145)..(5232)
<223> OTHER INFORMATION: exon 6
<220> FEATURE:
<221> NAME/KEY: CDS
<222> LOCATION: (7334)..(7421)
<223> OTHER INFORMATION: exon 7
<220> FEATURE:
<221> NAME/KEY: CDS
<222> LOCATION: (7517)..(8125)
<223> OTHER INFORMATION: exon 8

<400> SEQUENCE: 1
ggatccaccc acctcggcct cccaaagtgc tgggattaca ggcatgagca ctgtgcatgg      60
```

```
actatttatt tatttttttg aaacagagtt tcaatcttgt tgcacagcct ggagtgcaat      120
ggtgtgatct cagctcactg caacctctgc cttctggttt caagcaattc tcctgcctca      180
gcctcctgag tagctgggat tacaggcacc caccaccacg ctcgaatata tatatatatt      240
ttttgagacg gagtccgctc tgtcaccagg ctggagtgca gtggccaaat atcggctcac      300
tgaaacctcc ggctcctggg ttcaagcgat tctcctgcag cctcccaagt agctgggatt      360
acaggcatgc agcaccacgc ccatctaatt tttgtatttt tggtagagat ggggttttac      420
catgttggcc aggatggtct tgatctcttg acctcgtgat ctgcccacct cggcctccca      480
aagtgctggg attacaggcg tgacgaccgc gcccggccta cgcctggcta attttttgtat      540 ttttagtaga cgtggtttt cgccatgttg cccaggctgg tctcgaactc ctgacctcat      600
gatccgcctg tctcggcctc ccaaagtgtt gggattacaa gtatgagcca ccgcgccact      660 agccaattt ttttattttt tgagatgcag tctcactctg ttgcccaggc tggagttgca      720
gtggcatgat cttggctcac tgcaatcttc atctcccaga ctgaagcagt tctcatgcct      780
cagcctcctg agtagctggg attacagcac acgccaccac acctggctaa ttttttgtatt      840 tttagtagag atgggatttc accatgttgg ccaggctggt ctcaaactcc tgacctcaag      900
tgatttgccc acgtcggcct cccaaagtgc tgggattata ggcgtgagcc accgccagc      960 ccaagagaat aaaaatgtgg gtggtaaaaa ttttttttccc aaaaattcgt aaatgaaaat     1020
ctcacatatt atgcatactg cccaggagca tggcctagca ctgtgcaaac actcaactgc     1080
tggtcgttgc aaggattatt attggccggc ttcagtggct tgctggtatt cccagcacat     1140
tgggagatgg aggctggagg attgcttaag tccgggattt caagaccagc ctggacaaca     1200
tagtgggatc ccatctctac aaagaatttt aaaaattagc caggtgcagt gggaagattg     1260
cttcagtcca gaggctgcag tgagctatga ttgtgccact gcactccagc ctgggtgaca     1320
gagcaacacc ctgagacaga gagagagagg gggaaggagg gaaggaggga aggaaggaag     1380
gaaggaagga aggaaggaag gaaggaagga aggaaggaaa ggagagagag agagagagag     1440
agagagagag agagagaaaa taattttttat ttatttccag gctgggaaga gatgctgatt     1500
tctgcgataa aatcagtagg tacatttttt ggaatgttcg ctatgtgcca ggctagattt     1560
tacagatgag aagtctgaag ctcaggtaag gtaagtcacc tgtccagggc cacaaagaaa     1620
aaaaaaacgt gtgtctgaag ccagaacggg agctgttgcg cccaactccc tcccctgccc     1680
ccaagcggcc tctgggctcg ggaagggccc ctgcctcctc ccgccaggca cttatctcta     1740
cccaggctga gtgctggccc cgcccctcgg ggatctgcca cttagaggcg cctggtcggg     1800
aagggcctgg tcagctgcgt ccggcggagg cagctgctga cccagctgtg gactgtgccg     1860
ggggtggggg acggagggggc aggagccctg ggctccccgt ggcgggggct gtatc atg     1918
                                                                Met
                                                                  1 gac cac ctc ggg gcg tcc ctc tgg ccc cag gtc ggc tcc ctt tgt ctc     1966
Asp His Leu Gly Ala Ser Leu Trp Pro Gln Val Gly Ser Leu Cys Leu
      5                  10                 15 ctg ctc gct ggg gcc gcc tgg gcg ccc ccg cct aac ctc ccg gac ccc     2014
Leu Leu Ala Gly Ala Ala Trp Ala Pro Pro Pro Asn Leu Pro Asp Pro
        20                  25                  30 aag ttc gag agc aaa g gtaaggatga gctgcgtgtg gaccccctacg ctggagcctg     2070
Lys Phe Glu Ser Lys
  35 caggaccatg ctggggcctg aactcccagc ctaggtcctg ggggccatgc tgtttctgga     2130 cttcctgacc gggtcctggg ggccaagctg gcatctgaac ccttagactg ggtcctggat     2190
```

```
gggtggggggg cggggtgggg tatgttagga tccaagactc ctgatcgcgt cccgggcaag     2250
agctagagtg ggcttaacat tcccgttttta ccttttcagg gagtctggga catgctaaat     2310 cctaagggg ctgacttggt gctaaggtcc ctgggggtg gggaccaagc cgatccctag       2370
gggagggagg gtaaagcccg ggtccgagtt agagggccaa gccacaggct actgtaaaca     2430
cggtttgtgt gagggcgcca gatcacttgc ccggcccgt ggaggagg aggcgggggg         2490 cacggttggc gctatcggtt ggcggggagc ctgccggggc cgatagggg cccgcctctc      2550 cgcacacacc cccagccgcg cgcgtgtcct aggctgggc ggggctggca gtcccgagct     2610
cgaggtcttg aacgccgcgc ccagctcagc tggccgctgg gtgggcaggt gtgcgccagt    2670
ggtgcacggc gggggacagt aaggcgagaa acttgccct gggaattagg ggggcaccac     2730
ctctgcggac ccctccaagg gacccgcttg ggaagatggc agggcgggc ttttttctta     2790 tcgggtccgc ccaggctgcg ggagggaaga ggaggggct gtctcccgag atagagctc      2850 agaccccat gcccttcctt tgtcgcccct ccccag cg gcc ttg ctg gcg gcc         2903
                                          Ala Ala Leu Leu Ala Ala
                                                   40 cgg ggg ccc gaa gag ctt ctg tgc ttc acc gag cgg ttg gag gac ttg       2951
Arg Gly Pro Glu Glu Leu Leu Cys Phe Thr Glu Arg Leu Glu Asp Leu
45              50                  55                  60 gtg tgt ttc tgg gag gaa gcg gcg agc gct ggg gtg ggc ccg ggc aac       2999
Val Cys Phe Trp Glu Glu Ala Ala Ser Ala Gly Val Gly Pro Gly Asn
                65                  70                  75 tac agc ttc tcc tac cag ctc ga  gtgagtccga tccggcgggt gcctccaagg       3052
Tyr Ser Phe Ser Tyr Gln Leu Glu
                80 gcggagggag ggggtggggc agagctccct ggaggtcgta gcctcgtatg tcccctgctg     3112 tttgaggccc gacggcgcct ccagtcgtgg tcactggagg gaaacctgcg ggtccagggc    3172 tggcacgcct ctatgggccg gggcgcgaac actcccgcga tcaccgctgg aacgcgaccc    3232 caaacatcag gctgggataa caacgcctcc aaatcgaggg taaggcgtta ctacgtcggg    3292 gctgggacgc cttctcgagg tagtatccaa aaggaggcca gcagtgctca tgcctgtaat    3352 cccaactctt tggaaggtcg agcggaagaa ccgcttgagc ccaggtgttc aagaccagcc    3412 tgggcaacac agcgagatcc ccgtctctta aaaaaaatt agactgggcg cggctgcacg     3472 cctgtaatcc cagcactttg ggaggctgag gcgggcggat cacctgaggt cgggagtttg    3532 agagccagcc tggccaacat ggagaaactc tatctctact aaaaatacaa aattagccgg    3592 gcgtggtggc gcatgcctgt gatcccagct actcggagg ctgaggcagg agaatcgctt     3652 gaacccggga ggcggaggtt gcggtgagcc gaggtagcgc cattgcactc cagcctgggc   3712 aacaagagcg aaactccgtc tcaaaaaaaa aaaaataaa agccaggcgt ggcgcgtgcc    3772 tgtggtctca actacttggg aagctgaggt gggaggatcc cttaagcccc agaatttgag    3832 gctgcagtga gccatgatcg cgccactgca ctccagcctg ggcgacgaag gaacaccttg   3892 tcacacacac acacaaggct agaccttgtg tcacacatac acactgcccc ccacaggccg   3952 ggcaatgcca actcccggt ccccctccc aacctgctcc cttccctggg cgcatag g        4010 gat gag cca tgg aag ctg tgt cgc ctg cac cag gct ccc acg gct cgt       4058
Asp Glu Pro Trp Lys Leu Cys Arg Leu His Gln Ala Pro Thr Ala Arg
85              90                  95                  100 ggt gcg gtg cgc ttc tgg tgt tcg ctg cct aca gcc gac acg tcg agc       4106
Gly Ala Val Arg Phe Trp Cys Ser Leu Pro Thr Ala Asp Thr Ser Ser
            105                 110                 115 ttc gtg ccc cta gag ttg cgc gtc aca gca gcc tcc ggc gct ccg cga       4154
```

```
                                                                    -continued Phe Val Pro Leu Glu Leu Arg Val Thr Ala Ala Ser Gly Ala Pro Arg
        120                 125                 130 tat cac cgt gtc atc cac atc aat gaa gta g gtaagtgctc tgggaatgga      4205
Tyr His Arg Val Ile His Ile Asn Glu Val
        135                 140 ggagtggtcg gaggagaggg tctcagtcct cgcccacctg accaaccccc atgcctgcag    4265 tg  ctc cta gac gcc ccc gtg ggg ctg gtg gcg cgg ttg gct gac gag      4312
Val Leu Leu Asp Ala Pro Val Gly Leu Val Ala Arg Leu Ala Asp Glu
        145                 150                 155 agc ggc cac gta gtg ttg cgc tgg ctc ccg ccg cct gag aca ccc atg      4360
Ser Gly His Val Val Leu Arg Trp Leu Pro Pro Pro Glu Thr Pro Met
    160                 165                 170 acg tct cac atc cgc tac gag gtg gac gtc tcg gcc ggc aac ggc gca      4408
Thr Ser His Ile Arg Tyr Glu Val Asp Val Ser Ala Gly Asn Gly Ala
175                 180                 185                 190 ggg agc gta cag agg gtgaggccag ccctacggc ccagccccca aagctccact       4463
Gly Ser Val Gln Arg
                195 gactacggcc cagccacgcc tctcgaggtc gcgcccggtg ccgctttcag ggccggtccg    4523 taacatccca catcccatta ccctggtgct gaagaccgtt ccacgccac agacacagcc     4583 cccttttccta atgtcctcgc aagcctgttg aacccccaact tcttctccct ccggcccgta  4643 accctagacc cctttagcgc ccgggtccct ctacgagtgc tagcccagat attaaattgc    4703 ccgggtcccg ccctttcgta ccagagactc tctctctgat tggccctgag ctttcttggg   4763 ctcctccccc tactcttatt ggtcccattg caattctagg gcaccgtttt cctttccccct  4823 gattggctca gttccaccag ggcccgcccc cacgtcatct attttttgtct gctacgcgtc   4883 cctcgccctg attccgcccc cag gtg gag atc ctg gag ggc cgc acc gag tgt    4936
                          Val Glu Ile Leu Glu Gly Arg Thr Glu Cys
                                          200                 205 gtg ctg agc aac ctg cgg ggc cgg acg cgc tac acc ttc gcc gtc cgc      4984
Val Leu Ser Asn Leu Arg Gly Arg Thr Arg Tyr Thr Phe Ala Val Arg
            210                 215                 220 gcg cgt atg gct gag ccg agc ttc ggc ggc ttc tgg agc gcc tgg tcg      5032
Ala Arg Met Ala Glu Pro Ser Phe Gly Gly Phe Trp Ser Ala Trp Ser
225                 230                 235 gag cct gtg tcg ctg ctg acg cct agc g gtgaggcccc aggcggggt           5080
Glu Pro Val Ser Leu Leu Thr Pro Ser
        240                 245 gtaggaggag ccagggcgaa tcacggggca gcccaccgc cctgacctcc tccccgcctc     5140 ttag ac ctg gac ccc ctc atc ctg acg ctc tcc ctc atc ctc gtg gtc     5188
     Asp Leu Asp Pro Leu Ile Leu Thr Leu Ser Leu Ile Leu Val Val
                 250                 255                 260 atc ctg gtg ctg ctg acc gtg ctc gcg ctg ctc tcc cac cgc cg          5232
Ile Leu Val Leu Leu Thr Val Leu Ala Leu Leu Ser His Arg Arg
        265                 270                 275 gtgagctccc catttgggcg ctgggcccag actcctcccc gccaacggtc ctctttcact   5292
atggaaacct aggctcagag agagacacgc acttgcccaa ggtcacgcag taaggattca   5352
catcagtggc agggctggga tgcatgccag actagaccca gactcttcgt taacattttc   5412
tgctcttggg gactttcacc tgatttttcct tctacatcag gggctgccat ttcttgggtc  5472
cctttgttag ttcctttccc cagtgtcatc acctttgtaa aatcaactag atggatttag   5532
tgaaagaatt taagaccctg aatgcctccg caccctgcg gtcaagcttc tcagacacta    5592
tgatcagact agccgttctg aggtatttgt aattccaagc acacactagg tggtttcaca   5652
cccccaagct tttgcccatg ctgttccctc tgcctggaat gcccttcctg ccttgtctgc   5712
```

```
taagcaatct tctagtcgtc tttcatggcc ctgttcattt acttggttgg aaaatacaaa      5772
cagagtgcca aacatgtgcc aggcactgga gagagaatgg agaacaagct agaccctgac      5832
cacaagtccc tgaccttgtg gatctcaagt caacaaacaa gggacccaag aaatatttga      5892
tgacaaattg taatgagtga tatcacagaa acaaacagaa tgtggtgaca tgacaggatg      5952
gtcagggaag gctccaggag gaggtgacat cagagtggaa acctgaagat tggaaggaag      6012
cagccgcttg aaaagtgggg agaagaaaca gcaagtgcaa aggccctgag gtgggaatga      6072
gattggaacg ttcagccagc ttcaagaatt gccacatgca tggcctggca tggtggctca      6132
cgcctgtaat cccagcactt tgggatgccg aggcaggcag atcacctgag gttgggagtt      6192
cgcgaccagc ctgaccaaca tggagaaacc ccacctctac taaaaataca aaactagcca      6252
agcgtggtgg cacatgcctg taatccccgc tactcgggag gctgaggcag gagaatcact      6312
tgaacctggg aggtggaggt tgcgggtgag ccgagatcgt gccatcgcat tccagcctgg      6372
gcaataagag tgaaactccg tctcaaaaaa aaaaaaaaaa ttgccacatg ctagagtgg      6432 tatgtaaggg ggtgtggcag atattgagat gagggaggtg acaggggtca tataacgcag      6492
ggccttctgc agggtggtgg ggaggagttt ggaattttt ttttttttga cagagtca       6552 ctcttgtcgc ccaagctgta gtgcagtgca gcagtcttgg ctcactgcaa ctctgcctcc      6612
caggttcaag tgattctcct gcctcaaccg cctgagtagc tgagattaca ggcgtgcatg      6672
cccggctaat tttgtagttt tagtagagac ggggttccac catgttggcc aggctggtct      6732
caaactcctg acctcaggtg atctgctcac atcagcctct caaagtgctg ggattatagg      6792
catgagccac cgtgcctggc ttggatttta tcctaaatgc ctctctcatt accccagaag      6852
gtaacataat atttatctat gaagtgacat catggacctc ctggaaaaat ctgggccagg      6912
gttttgggtt ttttaattta ttttatttta ttttttttag agatgggggt ctcactatgt      6972
ttcctaggct ggtcttgaac tcctgggttc aaatgatcct cccacctcag cctcccaaag      7032
tactgggatt atagtgctgg tgtaaaccac tgcacctggc catggccagg attaaaggga      7092
gaatgaccaa ggtatattga actcctatgc acccttcaat accctgttcc atttacccttt    7152 ttgtagggcc ttgctgatgc ttcagccaaa acccctgtcc cctggccctg atgtactcct      7212
ctgcctccat tgtgatcaca gggaccaagt gtatctgtgc ctctatgact gggagtggag      7272
ggggaattgg tgagtattca atgagtcata tctatgtaac tatttatatt ggcttcaaca      7332
```

| | | | | | | | | | | | | |
|---|---|---|---|---|---|---|---|---|---|---|---|---|
| g g gct | ctg | aag | cag | aag | atc | tgg | cct | ggc | atc | ccg | agc | cca gag agc | 7379 |
| Ala | Leu | Lys | Gln | Lys | Ile | Trp | Pro | Gly | Ile | Pro | Ser | Pro Glu Ser |
| | | 280 | | | | 285 | | | | 290 | | |

```
gag ttt gaa ggc ctc ttc acc acc cac aag ggt aac ttc cag                7421
Glu Phe Glu Gly Leu Phe Thr Thr His Lys Gly Asn Phe Gln
    295                 300                 305 gtaggtggcc tggttgtccc ctcagtgcct gggcttccct gcttcttgca gccaaactgc      7481
aggcctctct gagcaggttg gtgctatttc ttcag ctg tgg ctg tac cag aat        7534
                                       Leu Trp Leu Tyr Gln Asn
                                                         310 gat ggc tgc ctg tgg tgg agc ccc tgc acc ccc ttc acg gag gac cca        7582
Asp Gly Cys Leu Trp Trp Ser Pro Cys Thr Pro Phe Thr Glu Asp Pro
        315                 320                 325 cct gct tcc ctg gaa gtc ctc tca gag cgc tgc tgg ggg acg atg cag        7630
Pro Ala Ser Leu Glu Val Leu Ser Glu Arg Cys Trp Gly Thr Met Gln
        330                 335                 340 gca gtg gag ccg ggg aca gat gat gag ggc ccc ctg ctg gag cca gtg        7678
Ala Val Glu Pro Gly Thr Asp Asp Glu Gly Pro Leu Leu Glu Pro Val
    345                 350                 355
```

```
ggc agt gag cat gcc cag gat acc tat ctg gtg ctg gac aaa tgg ttg    7726
Gly Ser Glu His Ala Gln Asp Thr Tyr Leu Val Leu Asp Lys Trp Leu
360                 365                 370                 375 ctg ccc cgg aac ccg ccc agt gag gac ctc cca ggg cct ggt ggc agt    7774
Leu Pro Arg Asn Pro Pro Ser Glu Asp Leu Pro Gly Pro Gly Gly Ser
            380                 385                 390 gtg gac ata gtg gcc atg gat gaa ggc tca gaa gca tcc tcc tgc tca    7822
Val Asp Ile Val Ala Met Asp Glu Gly Ser Glu Ala Ser Ser Cys Ser
        395                 400                 405 tct gct ttg gcc tcg aag ccc agc cca gag gga gcc tct gct gcc agc    7870
Ser Ala Leu Ala Ser Lys Pro Ser Pro Glu Gly Ala Ser Ala Ala Ser
    410                 415                 420 ttt gag tac act atc ctg gac ccc agc tcc cag ctc ttg cgt cca tgg    7918
Phe Glu Tyr Thr Ile Leu Asp Pro Ser Ser Gln Leu Leu Arg Pro Trp
425                 430                 435 aca ctg tgc cct gag ctg ccc cct acc cca ccc cac cta aag tac ctg    7966
Thr Leu Cys Pro Glu Leu Pro Pro Thr Pro Pro His Leu Lys Tyr Leu
440                 445                 450                 455 tac ctt gtg gta tct gac tct ggc atc tca act gac tac agc tca ggg    8014
Tyr Leu Val Val Ser Asp Ser Gly Ile Ser Thr Asp Tyr Ser Ser Gly
                460                 465                 470 gac tcc cag gga gcc caa ggg ggc tta tcc gat ggc ccc tac tcc aac    8062
Asp Ser Gln Gly Ala Gln Gly Gly Leu Ser Asp Gly Pro Tyr Ser Asn
            475                 480                 485 cct tat gag aac agc ctt atc cca gcc gct gag cct ctg ccc ccc agc    8110
Pro Tyr Glu Asn Ser Leu Ile Pro Ala Ala Glu Pro Leu Pro Pro Ser
        490                 495                 500 tat gtg gct tgc tct taggacacca ggctgcagat gatcagggat ccaatatgac    8165
Tyr Val Ala Cys Ser
    505 tcagagaacc agtgcagact caagacttat ggaacaggga tggcgaggcc tctctcagga  8225 gcagggcat tgctgatttt gtctgcccaa tccatcctgc tcaggaaacc acaaccttgc   8285 agtattttta aatatgtata gttttttttt gtatctatat atatatatac acatatgtat  8345 gtaagttttt ctaccatgat ttctacaaac accctttaag tcccatcttc ccctgggcat  8405 aggccatagg gatagaagtt aaagttcttg agcttattca gaagctggat ctgcaatctg  8465 aatgctactc ataacataac aaaatagtat gttaaacagc tcttaaatct tactggctta  8525 ccacattaaa tgatttctct ctcctaactc agctcaaatg ggcagccatc catggatgag  8585 tcagaggttc agactcttcc agtctgtagc tctaccttct cttagggtac ttagatggat  8645 cc                                                                 8647

<210> SEQ ID NO 2
<211> LENGTH: 508
<212> TYPE: PRT
<213> ORGANISM: Homo sapiens

<400> SEQUENCE: 2

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
```

-continued

```
                65                  70                  75                  80
Tyr Gln Leu Glu Asp Glu Pro Trp Lys Leu Cys Arg Leu His Gln Ala
                    85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
                260                 265                 270

Ser His Arg Arg Ala Leu Lys Gln Lys Ile Trp Pro Gly Ile Pro Ser
            275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
    355                 360                 365

Leu Val Leu Asp Lys Trp Leu Leu Pro Arg Asn Pro Pro Ser Glu Asp
370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
    435                 440                 445

Pro Pro His Leu Lys Tyr Leu Tyr Leu Val Val Ser Asp Ser Gly Ile
450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495
```

Ala Glu Pro Leu Pro Pro Ser Tyr Val Ala Cys Ser
                500                 505

<210> SEQ ID NO 3
<211> LENGTH: 1865
<212> TYPE: DNA
<213> ORGANISM: Homo sapiens
<220> FEATURE:
<221> NAME/KEY: misc_feature
<222> LOCATION: (1)..(1865)
<223> OTHER INFORMATION: Mature full-length EpoR mRNA
<220> FEATURE:
<221> NAME/KEY: misc_feature
<222> LOCATION: (137)..(1660)
<223> OTHER INFORMATION: Full-length EpoR ORF

<400> SEQUENCE: 3

```
acttagaggc gcctggtcgg gaagggcctg gtcagctgcg tccggcggag gcagctgctg      60
acccagctgt ggactgtgcc ggggtgggg gacggagggg caggagccct gggctccccg     120
tggcggggc tgtatcatgg accacctcgg ggcgtccctc tggccccagg tcggctccct    180
ttgtctcctg ctcgctgggg ccgcctgggc gccccgcct aacctcccgg accccaagtt    240
cgagagcaaa gcggccttgc tggcggcccg ggggcccgaa gagcttctgt gcttcaccga    300
gcggttggag gacttggtgt gtttctggga ggaagcggcg agcgctgggg tgggcccggg    360
caactacagc ttctcctacc agctcgagga tgagccatgg aagctgtgtc gcctgcacca    420
ggctcccacg gctcgtggtg cggtgcgctt ctggtgttcg ctgcctacag ccgacacgtc    480
gagcttcgtg ccctagagt gcgcgtcac agcagcctcc ggcgctccgc gatatcaccg    540
tgtcatccac atcaatgaag tagtgctcct agacgccccc gtgggctgg tggcgcggtt    600
ggctgacgag agcggccacg tagtgttgcg ctggctcccg ccgcctgaga cacccatgac    660
gtctcacatc cgctacgagg tggacgtctc ggccggcaac ggcgcaggga gcgtacagag    720
ggtggagatc ctggagggcc gcaccgagtg tgtgctgagc aacctgcggg gccggacgcg    780
ctacaccttc gccgtccgcg cgcgtatggc tgagccgagc ttcggcggct ctggagcgc    840
ctggtcggag cctgtgtcgc tgctgacgcc tagcgacctg gaccccctca tcctgacgct    900
ctccctcatc ctcgtggtca tcctggtgct gctgaccgtg ctcgcgctgc tctcccaccg    960
ccgggctctg aagcagaaga tctggcctgg catcccgagc ccagagagcg agtttgaagg   1020
cctcttcacc acccacaagg gtaacttcca gctgtggctg taccagaatg atggctgcct   1080
gtggtggagc ccctgcaccc ccttcacgga ggacccacct gcttccctgg aagtcctctc   1140
agagcgctgc tggggacga tgcaggcagt ggagccgggg acagatgatg agggcccct    1200
gctggagcca gtgggcagtg agcatgccca ggatacctat ctggtgctgg acaaatggtt   1260
gctgccccgg aacccgccca gtgaggacct cccagggcct ggtggcagtg tggacatagt   1320
ggccatggat gaaggctcag aagcatcctc ctgctcatct gctttggcct cgaagcccag   1380
cccagaggga gcctctgctg ccagctttga gtacactatc ctggacccca gctcccagct   1440
cttgcgtcca tggacactgt gccctgagct gccccctacc ccaccccacc taaagtacct   1500
gtaccttgtg gtatctgact ctggcatctc aactgactac agctcagggg actcccaggg   1560
agcccaaggg ggcttatccg atggccccta ctccaaccct tatgagaaca gccttatccc   1620
agccgctgag cctctgcccc ccagctatgt ggcttgctct taggacacca ggctgcagat   1680
gatcagggat ccaatatgac tcagagaacc agtgcagact caagacttat ggaacaggga   1740
tggcgaggcc tctctcagga gcaggggcat tgctgatttt gtctgcccaa tccatcctgc   1800
tcaggaaacc acaaccttgc agtatttttt aaatatgtat gttttttat atgtatagtt   1860
``` ttttt                                                                    1865

<210> SEQ ID NO 4
<211> LENGTH: 858
<212> TYPE: DNA
<213> ORGANISM: Homo sapiens
<220> FEATURE:
<221> NAME/KEY: CDS
<222> LOCATION: (1)..(855)
<223> OTHER INFORMATION: EpoR Isoform 1, intron 6 insert

<400> SEQUENCE: 4

| | | | | | | | | | | | | | | | | |
|---|---|---|---|---|---|---|---|---|---|---|---|---|---|---|---|---|
| atg | gac | cac | ctc | ggg | gcg | tcc | ctc | tgg | ccc | cag | gtc | ggc | tcc | ctt | tgt | 48 |
| Met | Asp | His | Leu | Gly | Ala | Ser | Leu | Trp | Pro | Gln | Val | Gly | Ser | Leu | Cys | |
| 1 | | | | 5 | | | | | 10 | | | | | 15 | | |

| ctc | ctg | ctc | gct | ggg | gcc | gcc | tgg | gcg | ccc | ccg | cct | aac | ctc | ccg | gac | 96 |
|---|---|---|---|---|---|---|---|---|---|---|---|---|---|---|---|---|
| Leu | Leu | Leu | Ala | Gly | Ala | Ala | Trp | Ala | Pro | Pro | Pro | Asn | Leu | Pro | Asp | |
| | | | 20 | | | | | 25 | | | | | 30 | | | |

| ccc | aag | ttc | gag | agc | aaa | gcg | gcc | ttg | ctg | gcg | gcc | cgg | ggg | ccc | gaa | 144 |
|---|---|---|---|---|---|---|---|---|---|---|---|---|---|---|---|---|
| Pro | Lys | Phe | Glu | Ser | Lys | Ala | Ala | Leu | Leu | Ala | Ala | Arg | Gly | Pro | Glu | |
| | 35 | | | | | 40 | | | | | 45 | | | | | |

| gag | ctt | ctg | tgc | ttc | acc | gag | cgg | ttg | gag | gac | ttg | gtg | tgt | ttc | tgg | 192 |
|---|---|---|---|---|---|---|---|---|---|---|---|---|---|---|---|---|
| Glu | Leu | Leu | Cys | Phe | Thr | Glu | Arg | Leu | Glu | Asp | Leu | Val | Cys | Phe | Trp | |
| 50 | | | | | 55 | | | | | 60 | | | | | | |

| gag | gaa | gcg | gcg | agc | gct | ggg | gtg | ggc | ccg | ggc | aac | tac | agc | ttc | tcc | 240 |
|---|---|---|---|---|---|---|---|---|---|---|---|---|---|---|---|---|
| Glu | Glu | Ala | Ala | Ser | Ala | Gly | Val | Gly | Pro | Gly | Asn | Tyr | Ser | Phe | Ser | |
| 65 | | | | | 70 | | | | | 75 | | | | | 80 | |

| tac | cag | ctc | gag | gat | gag | cca | tgg | aag | ctg | tgt | cgc | ctg | cac | cag | gct | 288 |
|---|---|---|---|---|---|---|---|---|---|---|---|---|---|---|---|---|
| Tyr | Gln | Leu | Glu | Asp | Glu | Pro | Trp | Lys | Leu | Cys | Arg | Leu | His | Gln | Ala | |
| | | | | 85 | | | | | 90 | | | | | 95 | | |

| ccc | acg | gct | cgt | ggt | gcg | gtg | cgc | ttc | tgg | tgt | tcg | ctg | cct | aca | gcc | 336 |
|---|---|---|---|---|---|---|---|---|---|---|---|---|---|---|---|---|
| Pro | Thr | Ala | Arg | Gly | Ala | Val | Arg | Phe | Trp | Cys | Ser | Leu | Pro | Thr | Ala | |
| | | | 100 | | | | | 105 | | | | | 110 | | | |

| gac | acg | tcg | agc | ttc | gtg | ccc | cta | gag | ttg | cgc | gtc | aca | gca | gcc | tcc | 384 |
|---|---|---|---|---|---|---|---|---|---|---|---|---|---|---|---|---|
| Asp | Thr | Ser | Ser | Phe | Val | Pro | Leu | Glu | Leu | Arg | Val | Thr | Ala | Ala | Ser | |
| | | 115 | | | | | 120 | | | | | 125 | | | | |

| ggc | gct | ccg | cga | tat | cac | cgt | gtc | atc | cac | atc | aat | gaa | gta | gtg | ctc | 432 |
|---|---|---|---|---|---|---|---|---|---|---|---|---|---|---|---|---|
| Gly | Ala | Pro | Arg | Tyr | His | Arg | Val | Ile | His | Ile | Asn | Glu | Val | Val | Leu | |
| | 130 | | | | | 135 | | | | | 140 | | | | | |

| cta | gac | gcc | ccc | gtg | ggg | ctg | gtg | gcg | cgg | ttg | gct | gac | gag | agc | ggc | 480 |
|---|---|---|---|---|---|---|---|---|---|---|---|---|---|---|---|---|
| Leu | Asp | Ala | Pro | Val | Gly | Leu | Val | Ala | Arg | Leu | Ala | Asp | Glu | Ser | Gly | |
| 145 | | | | | 150 | | | | | 155 | | | | | 160 | |

| cac | gta | gtg | ttg | cgc | tgg | ctc | ccg | ccg | cct | gag | aca | ccc | atg | acg | tct | 528 |
|---|---|---|---|---|---|---|---|---|---|---|---|---|---|---|---|---|
| His | Val | Val | Leu | Arg | Trp | Leu | Pro | Pro | Pro | Glu | Thr | Pro | Met | Thr | Ser | |
| | | | | 165 | | | | | 170 | | | | | 175 | | |

| cac | atc | cgc | tac | gag | gtg | gac | gtc | tcg | gcc | ggc | aac | ggc | gca | ggg | agc | 576 |
|---|---|---|---|---|---|---|---|---|---|---|---|---|---|---|---|---|
| His | Ile | Arg | Tyr | Glu | Val | Asp | Val | Ser | Ala | Gly | Asn | Gly | Ala | Gly | Ser | |
| | | | 180 | | | | | 185 | | | | | 190 | | | |

| gta | cag | agg | gtg | gag | atc | ctg | gag | ggc | cgc | acc | gag | tgt | gtg | ctg | agc | 624 |
|---|---|---|---|---|---|---|---|---|---|---|---|---|---|---|---|---|
| Val | Gln | Arg | Val | Glu | Ile | Leu | Glu | Gly | Arg | Thr | Glu | Cys | Val | Leu | Ser | |
| | | 195 | | | | | 200 | | | | | 205 | | | | |

| aac | ctg | cgg | ggc | cgg | acg | cgc | tac | acc | ttc | gcc | gtc | cgc | gcg | cgt | atg | 672 |
|---|---|---|---|---|---|---|---|---|---|---|---|---|---|---|---|---|
| Asn | Leu | Arg | Gly | Arg | Thr | Arg | Tyr | Thr | Phe | Ala | Val | Arg | Ala | Arg | Met | |
| | 210 | | | | | 215 | | | | | 220 | | | | | |

| gct | gag | ccg | agc | ttc | ggc | ggc | ttc | tgg | agc | gcc | tgg | tcg | gag | cct | gtg | 720 |
|---|---|---|---|---|---|---|---|---|---|---|---|---|---|---|---|---|
| Ala | Glu | Pro | Ser | Phe | Gly | Gly | Phe | Trp | Ser | Ala | Trp | Ser | Glu | Pro | Val | |
| 225 | | | | | 230 | | | | | 235 | | | | | 240 | |

| tcg | ctg | ctg | acg | cct | agc | gac | ctg | gac | ccc | ctc | atc | ctg | acg | ctc | tcc | 768 |
|---|---|---|---|---|---|---|---|---|---|---|---|---|---|---|---|---|
| Ser | Leu | Leu | Thr | Pro | Ser | Asp | Leu | Asp | Pro | Leu | Ile | Leu | Thr | Leu | Ser | |
| | | | | 245 | | | | | 250 | | | | | 255 | | |

| ctc | atc | ctc | gtg | gtc | atc | ctg | gtg | ctg | ctg | acc | gtg | ctc | gcg | ctg | ctc | 816 |

```
Leu Ile Leu Val Val Ile Leu Val Leu Leu Thr Val Leu Ala Leu Leu
            260                 265                 270 tcc cac cgc cgg atg gtc agg gaa ggc tcc agg agg agg tga              858
Ser His Arg Arg Met Val Arg Glu Gly Ser Arg Arg Arg
            275                 280                 285
```

<210> SEQ ID NO 5
<211> LENGTH: 285
<212> TYPE: PRT
<213> ORGANISM: Homo sapiens

<400> SEQUENCE: 5

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Met Val Arg Glu Gly Ser Arg Arg Arg
        275                 280                 285
```

<210> SEQ ID NO 6
<211> LENGTH: 954
<212> TYPE: DNA
<213> ORGANISM: Homo sapiens
<220> FEATURE:
<221> NAME/KEY: CDS
<222> LOCATION: (1)..(951)
<223> OTHER INFORMATION: EpoR Isoform 2, intron 7 insert

<400> SEQUENCE: 6

```
atg gac cac ctc ggg gcg tcc ctc tgg ccc cag gtc ggc tcc ctt tgt        48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac        96
Leu Leu Leu Ala Gly Ala Ala Trp Ala Pro Pro Pro Asn Leu Pro Asp
            20                  25                  30 ccc aag ttc gag agc aaa gcg gcc ttg ctg gcg gcc cgg ggg ccc gaa       144
Pro Lys Phe Glu Ser Lys Ala Ala Leu Leu Ala Ala Arg Gly Pro Glu
        35                  40                  45 gag ctt ctg tgc ttc acc gag cgg ttg gag gac ttg gtg tgt ttc tgg       192
Glu Leu Leu Cys Phe Thr Glu Arg Leu Glu Asp Leu Val Cys Phe Trp
50                  55                  60 gag gaa gcg gcg agc gct ggg gtg ggc ccg ggc aac tac agc ttc tcc       240
Glu Glu Ala Ala Ser Ala Gly Val Gly Pro Gly Asn Tyr Ser Phe Ser
65                  70                  75                  80 tac cag ctc gag gat gag cca tgg aag ctg tgt cgc ctg cac cag gct       288
Tyr Gln Leu Glu Asp Glu Pro Trp Lys Leu Cys Arg Leu His Gln Ala
                85                  90                  95 ccc acg gct cgt ggt gcg gtg cgc ttc tgg tgt tcg ctg cct aca gcc       336
Pro Thr Ala Arg Gly Ala Val Arg Phe Trp Cys Ser Leu Pro Thr Ala
            100                 105                 110 gac acg tcg agc ttc gtg ccc cta gag ttg cgc gtc aca gca gcc tcc       384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc       432
Gly Ala Pro Arg Tyr His Arg Val Ile His Ile Asn Glu Val Val Leu
130                 135                 140 cta gac gcc ccc gtg ggg ctg gtg gcg cgg ttg gct gac gag agc ggc       480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct       528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc       576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc       624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg       672
Asn Leu Arg Gly Arg Thr Arg Tyr Thr Phe Ala Val Arg Ala Arg Met
210                 215                 220 gct gag ccg agc ttc ggc ggc ttc tgg agc gcc tgg tcg gag cct gtg       720
Ala Glu Pro Ser Phe Gly Gly Phe Trp Ser Ala Trp Ser Glu Pro Val
225                 230                 235                 240 tcg ctg ctg acg cct agc gac ctg gac ccc ctc atc ctg acg ctc tcc       768
Ser Leu Leu Thr Pro Ser Asp Leu Asp Pro Leu Ile Leu Thr Leu Ser
                245                 250                 255 ctc atc ctc gtg gtc atc ctg gtg ctg ctg acc gtg ctc gcg ctg ctc       816
Leu Ile Leu Val Val Ile Leu Val Leu Leu Thr Val Leu Ala Leu Leu
            260                 265                 270 tcc cac cgc cgg gct ctg aag cag aag atc tgg cct ggc atc ccg agc       864
Ser His Arg Arg Ala Leu Lys Gln Lys Ile Trp Pro Gly Ile Pro Ser
        275                 280                 285 cca gag agc gag ttt gaa ggc ctc ttc acc acc cac aag ggt aac ttc       912
Pro Glu Ser Glu Phe Glu Gly Leu Phe Thr Thr His Lys Gly Asn Phe
290                 295                 300 cag gtt ggt gct att tct tca gct gtg gct gta cca gaa tga               954
Gln Val Gly Ala Ile Ser Ser Ala Val Ala Val Pro Glu
305                 310                 315
```

<210> SEQ ID NO 7
<211> LENGTH: 317
<212> TYPE: PRT
<213> ORGANISM: Homo sapiens

<400> SEQUENCE: 7

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Val Gly Ala Ile Ser Ser Ala Val Ala Val Pro Glu
305                 310                 315

<210> SEQ ID NO 8
<211> LENGTH: 987
<212> TYPE: DNA
<213> ORGANISM: Homo sapiens
<220> FEATURE:
<221> NAME/KEY: CDS
<222> LOCATION: (1)..(984)
<223> OTHER INFORMATION: EpoR Isoform 3, intron 7 unspliced

<400> SEQUENCE: 8

```
atg gac cac ctc ggg gcg tcc ctc tgg ccc cag gtc ggc tcc ctt tgt      48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac      96
Leu Leu Leu Ala Gly Ala Ala Trp Ala Pro Pro Pro Asn Leu Pro Asp
                20                  25                  30 ccc aag ttc gag agc aaa gcg gcc ttg ctg gcg gcc cgg ggg ccc gaa     144
Pro Lys Phe Glu Ser Lys Ala Ala Leu Leu Ala Ala Arg Gly Pro Glu
            35                  40                  45 gag ctt ctg tgc ttc acc gag cgg ttg gag gac ttg gtg tgt ttc tgg     192
Glu Leu Leu Cys Phe Thr Glu Arg Leu Glu Asp Leu Val Cys Phe Trp
        50                  55                  60 gag gaa gcg gcg agc gct ggg gtg ggc ccg ggc aac tac agc ttc tcc     240
Glu Glu Ala Ala Ser Ala Gly Val Gly Pro Gly Asn Tyr Ser Phe Ser
65                  70                  75                  80 tac cag ctc gag gat gag cca tgg aag ctg tgt cgc ctg cac cag gct     288
Tyr Gln Leu Glu Asp Glu Pro Trp Lys Leu Cys Arg Leu His Gln Ala
                85                  90                  95 ccc acg gct cgt ggt gcg gtg cgc ttc tgg tgt tcg ctg cct aca gcc     336
Pro Thr Ala Arg Gly Ala Val Arg Phe Trp Cys Ser Leu Pro Thr Ala
            100                 105                 110 gac acg tcg agc ttc gtg ccc cta gag ttg cgc gtc aca gca gcc tcc     384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc     432
Gly Ala Pro Arg Tyr His Arg Val Ile His Ile Asn Glu Val Val Leu
    130                 135                 140 cta gac gcc ccc gtg ggg ctg gtg gcg cgg ttg gct gac gag agc ggc     480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct     528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc     576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc     624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg     672
Asn Leu Arg Gly Arg Thr Arg Tyr Thr Phe Ala Val Arg Ala Arg Met
    210                 215                 220 gct gag ccg agc ttc ggc ggc ttc tgg agc gcc tgg tcg gag cct gtg     720
Ala Glu Pro Ser Phe Gly Gly Phe Trp Ser Ala Trp Ser Glu Pro Val
225                 230                 235                 240 tcg ctg ctg acg cct agc gac ctg gac ccc ctc atc ctg acg ctc tcc     768
Ser Leu Leu Thr Pro Ser Asp Leu Asp Pro Leu Ile Leu Thr Leu Ser
                245                 250                 255 ctc atc ctc gtg gtc atc ctg gtg ctg ctg acc gtg ctc gcg ctg ctc     816
Leu Ile Leu Val Val Ile Leu Val Leu Leu Thr Val Leu Ala Leu Leu
            260                 265                 270 tcc cac cgc cgg gct ctg aag cag aag atc tgg cct ggc atc ccg agc     864
Ser His Arg Arg Ala Leu Lys Gln Lys Ile Trp Pro Gly Ile Pro Ser
        275                 280                 285 cca gag agc gag ttt gaa ggc ctc ttc acc acc cac aag ggt aac ttc     912
Pro Glu Ser Glu Phe Glu Gly Leu Phe Thr Thr His Lys Gly Asn Phe
    290                 295                 300 cag gta ggt ggc ctg gtt gtc ccc tca gtg cct ggg ctt ccc tgc ttc     960
Gln Val Gly Gly Leu Val Val Pro Ser Val Pro Gly Leu Pro Cys Phe
305                 310                 315                 320
```

```
ttg cag cca aac tgc agg cct ctc tga                                       987
Leu Gln Pro Asn Cys Arg Pro Leu
            325

<210> SEQ ID NO 9
<211> LENGTH: 328
<212> TYPE: PRT
<213> ORGANISM: Homo sapiens

<400> SEQUENCE: 9

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Val Gly Gly Leu Val Val Pro Ser Val Pro Gly Leu Pro Cys Phe
305                 310                 315                 320

Leu Gln Pro Asn Cys Arg Pro Leu
            325

<210> SEQ ID NO 10
<211> LENGTH: 804
<212> TYPE: DNA
```

<213> ORGANISM: Homo sapiens
<220> FEATURE:
<221> NAME/KEY: CDS
<222> LOCATION: (1)..(801)
<223> OTHER INFORMATION: EpoR Isoform 4, intron 5 unspliced

<400> SEQUENCE: 10

```
atg gac cac ctc ggg gcg tcc ctc tgg ccc cag gtc ggc tcc ctt tgt    48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac    96
Leu Leu Leu Ala Gly Ala Ala Trp Ala Pro Pro Pro Asn Leu Pro Asp
            20                  25                  30 ccc aag ttc gag agc aaa gcg gcc ttg ctg gcg gcc cgg ggg ccc gaa   144
Pro Lys Phe Glu Ser Lys Ala Ala Leu Leu Ala Ala Arg Gly Pro Glu
        35                  40                  45 gag ctt ctg tgc ttc acc gag cgg ttg gag gac ttg gtg tgt ttc tgg   192
Glu Leu Leu Cys Phe Thr Glu Arg Leu Glu Asp Leu Val Cys Phe Trp
    50                  55                  60 gag gaa gcg gcg agc gct ggg gtg ggc ccg ggc aac tac agc ttc tcc   240
Glu Glu Ala Ala Ser Ala Gly Val Gly Pro Gly Asn Tyr Ser Phe Ser
65                  70                  75                  80 tac cag ctc gag gat gag cca tgg aag ctg tgt cgc ctg cac cag gct   288
Tyr Gln Leu Glu Asp Glu Pro Trp Lys Leu Cys Arg Leu His Gln Ala
                85                  90                  95 ccc acg gct cgt ggt gcg gtg cgc ttc tgg tgt tcg ctg cct aca gcc   336
Pro Thr Ala Arg Gly Ala Val Arg Phe Trp Cys Ser Leu Pro Thr Ala
            100                 105                 110 gac acg tcg agc ttc gtg ccc cta gag ttg cgc gtc aca gca gcc tcc   384
Asp Thr Ser Ser Phe Val Pro Leu Glu Leu Arg Val Thr Ala Ala Ser
        115                 120                 125 ggc gct ccg cga tat cac cgt gtc atc cac atc aat gaa gta gtg ctc   432
Gly Ala Pro Arg Tyr His Arg Val Ile His Ile Asn Glu Val Val Leu
    130                 135                 140 cta gac gcc ccc gtg ggg ctg gtg gcg cgg ttg gct gac gag agc ggc   480
Leu Asp Ala Pro Val Gly Leu Val Ala Arg Leu Ala Asp Glu Ser Gly
145                 150                 155                 160 cac gta gtg ttg cgc tgg ctc ccg ccg cct gag aca ccc atg acg tct   528
His Val Val Leu Arg Trp Leu Pro Pro Pro Glu Thr Pro Met Thr Ser
                165                 170                 175 cac atc cgc tac gag gtg gac gtc tcg gcc ggc aac ggc gca ggg agc   576
His Ile Arg Tyr Glu Val Asp Val Ser Ala Gly Asn Gly Ala Gly Ser
            180                 185                 190 gta cag agg gtg gag atc ctg gag ggc cgc acc gag tgt gtg ctg agc   624
Val Gln Arg Val Glu Ile Leu Glu Gly Arg Thr Glu Cys Val Leu Ser
        195                 200                 205 aac ctg cgg ggc cgg acg cgc tac acc ttc gcc gtc cgc gcg cgt atg   672
Asn Leu Arg Gly Arg Thr Arg Tyr Thr Phe Ala Val Arg Ala Arg Met
    210                 215                 220 gct gag ccg agc ttc ggc ggc ttc tgg agc gcc tgg tcg gag cct gtg   720
Ala Glu Pro Ser Phe Gly Gly Phe Trp Ser Ala Trp Ser Glu Pro Val
225                 230                 235                 240 tcg ctg ctg acg cct agc ggt gag gcc cca ggg ggt gta gga gga       768
Ser Leu Leu Thr Pro Ser Gly Glu Ala Pro Gly Gly Val Gly Gly
                245                 250                 255 gcc agg gcg aat cac ggg gca agc cca ccg ccc tga                   804
Ala Arg Ala Asn His Gly Ala Ser Pro Pro Pro
            260                 265
```

<210> SEQ ID NO 11
<211> LENGTH: 267
<212> TYPE: PRT

<213> ORGANISM: Homo sapiens

<400> SEQUENCE: 11

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
            35                  40                  45

Glu Leu Leu Cys Phe Thr Glu Arg Leu Glu Asp Leu Val Cys Phe Trp
50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Arg Ala Arg Met
210                 215                 220

Ala Glu Pro Ser Phe Gly Gly Phe Trp Ser Ala Trp Ser Glu Pro Val
225                 230                 235                 240

Ser Leu Leu Thr Pro Ser Gly Glu Ala Pro Gly Gly Val Gly Gly
            245                 250                 255

Ala Arg Ala Asn His Gly Ala Ser Pro Pro Pro
            260                 265

<210> SEQ ID NO 12
<211> LENGTH: 747
<212> TYPE: DNA
<213> ORGANISM: Homo sapiens
<220> FEATURE:
<221> NAME/KEY: CDS
<222> LOCATION: (1)..(744)
<223> OTHER INFORMATION: EpoR Isoform 5, exon 6 skipped

<400> SEQUENCE: 12

```
atg gac cac ctc ggg gcg tcc ctc tgg ccc cag gtc ggc tcc ctt tgt      48
Met Asp His Leu Gly Ala Ser Leu Trp Pro Gln Val Gly Ser Leu Cys
1               5                   10                  15 ctc ctg ctc gct ggg gcc gcc tgg gcg ccc ccg cct aac ctc ccg gac      96
Leu Leu Leu Ala Gly Ala Ala Trp Ala Pro Pro Pro Asn Leu Pro Asp
            20                  25                  30 ccc aag ttc gag agc aaa gcg gcc ttg ctg gcg gcc cgg ggg ccc gaa     144
Pro Lys Phe Glu Ser Lys Ala Ala Leu Leu Ala Ala Arg Gly Pro Glu
            35                  40                  45 gag ctt ctg tgc ttc acc gag cgg ttg gag gac ttg gtg tgt ttc tgg     192
```

| | | |
|---|---|---|
| gag gaa gcg gcg agc gct ggg gtg ggc ccg ggc aac tac agc ttc tcc<br>Glu Glu Ala Ala Ser Ala Gly Val Gly Pro Gly Asn Tyr Ser Phe Ser<br>65                        70                         75                     80 | | 240 |
| tac cag ctc gag gat gag cca tgg aag ctg tgt cgc ctg cac cag gct<br>Tyr Gln Leu Glu Asp Glu Pro Trp Lys Leu Cys Arg Leu His Gln Ala<br>                        85                            90                         95 | | 288 |
| ccc acg gct cgt ggt gcg gtg cgc ttc tgg tgt tcg ctg cct aca gcc<br>Pro Thr Ala Arg Gly Ala Val Arg Phe Trp Cys Ser Leu Pro Thr Ala<br>                      100                        105                        110 | | 336 |
| gac acg tcg agc ttc gtg ccc cta gag ttg cgc gtc aca gca gcc tcc<br>Asp Thr Ser Ser Phe Val Pro Leu Glu Leu Arg Val Thr Ala Ala Ser<br>                      115                        120                        125 | | 384 |
| ggc gct ccg cga tat cac cgt gtc atc cac atc aat gaa gta gtg ctc<br>Gly Ala Pro Arg Tyr His Arg Val Ile His Ile Asn Glu Val Val Leu<br>130                        135                         140 | | 432 |
| cta gac gcc ccc gtg ggg ctg gtg gcg cgg ttg gct gac gag agc ggc<br>Leu Asp Ala Pro Val Gly Leu Val Ala Arg Leu Ala Asp Glu Ser Gly<br>145                        150                        155                        160 | | 480 |
| cac gta gtg ttg cgc tgg ctc ccg ccg cct gag aca ccc atg acg tct<br>His Val Val Leu Arg Trp Leu Pro Pro Pro Glu Thr Pro Met Thr Ser<br>                      165                        170                        175 | | 528 |
| cac atc cgc tac gag gtg gac gtc tcg gcc ggc aac ggc gca ggg agc<br>His Ile Arg Tyr Glu Val Asp Val Ser Ala Gly Asn Gly Ala Gly Ser<br>                      180                        185                        190 | | 576 |
| gta cag agg gtg gag atc ctg gag ggc cgc acc gag tgt gtg ctg agc<br>Val Gln Arg Val Glu Ile Leu Glu Gly Arg Thr Glu Cys Val Leu Ser<br>                195                        200                        205 | | 624 |
| aac ctg cgg ggc cgg acg cgc tac acc ttc gcc gtc cgc gcg cgt atg<br>Asn Leu Arg Gly Arg Thr Arg Tyr Thr Phe Ala Val Arg Ala Arg Met<br>210                        215                         220 | | 672 |
| gct gag ccg agc ttc ggc ggc ttc tgg agc gcc tgg tcg gag cct gtg<br>Ala Glu Pro Ser Phe Gly Gly Phe Trp Ser Ala Trp Ser Glu Pro Val<br>225                        230                        235                        240 | | 720 |
| tcg ctg ctg acg cct agc ggg ctc tga<br>Ser Leu Leu Thr Pro Ser Gly Leu<br>                      245 | | 747 |

<210> SEQ ID NO 13
<211> LENGTH: 248
<212> TYPE: PRT
<213> ORGANISM: Homo sapiens

<400> SEQUENCE: 13

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

```
Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
        130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Arg Ala Arg Met
210                 215                 220

Ala Glu Pro Ser Phe Gly Gly Phe Trp Ser Ala Trp Ser Glu Pro Val
225                 230                 235                 240

Ser Leu Leu Thr Pro Ser Gly Leu
                245

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
tcaagcggct gcttccttcc aa                                              22

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
gcagggagcg tacagagggt ggag                                            24

<210> SEQ ID NO 16
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 16
gaagaaatag caccaacctg gaag                                            24

<210> SEQ ID NO 17
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 17
ctgacgccta gcgacctgga cc                                              22

<210> SEQ ID NO 18
<211> LENGTH: 21
<212> TYPE: DNA
<213> ORGANISM: Artificial sequence
```

```
<220> FEATURE:
<223> OTHER INFORMATION: Synthetic oligonucleotide

<400> SEQUENCE: 18
gcagtttggc tgcaagaagc a                                           21

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ggagccaggg cgaatcacgg                                             20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gccttcaaac tcgctctctg                                             20

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
gcttcagagc ccgctaggcg t                                           21
```